United States Patent
Otteson et al.

(10) Patent No.: US 11,770,017 B2
(45) Date of Patent: Sep. 26, 2023

(54) SELF TUNING CLASS D DRIVER FOR MAXIMUM POWER FACTOR IN WIRELESS RECHARGER

(71) Applicant: Medtronic, Inc., Minneapolis, MN (US)

(72) Inventors: Brett Otteson, Minneapolis, MN (US); Charles M. Nowell, Jr., Longwood, FL (US); Michael J. Hage, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 201 days.

(21) Appl. No.: 17/077,425

(22) Filed: Oct. 22, 2020

(65) Prior Publication Data

US 2021/0126484 A1   Apr. 29, 2021

Related U.S. Application Data

(60) Provisional application No. 62/925,487, filed on Oct. 24, 2019.

(51) Int. Cl.
| | |
|---|---|
| *H02J 50/12* | (2016.01) |
| *H02J 7/04* | (2006.01) |
| *H02J 7/00* | (2006.01) |
| *A61N 1/36* | (2006.01) |
| *A61N 1/378* | (2006.01) |

(52) U.S. Cl.
CPC ............ *H02J 7/04* (2013.01); *H02J 50/12* (2016.02); *A61N 1/3605* (2013.01); *A61N 1/3787* (2013.01); *H02J 7/00712* (2020.01)

(58) Field of Classification Search
None
See application file for complete search history.

(56) References Cited

U.S. PATENT DOCUMENTS

| | | | |
|---|---|---|---|
| 5,095,224 A * | 3/1992 | Renger | H02M 7/53803 310/319 |
| 8,818,523 B2 * | 8/2014 | Olson | A61N 1/3787 320/108 |
| 9,744,368 B2 | 8/2017 | Dinsmoor | |
| 10,110,010 B2 | 10/2018 | Lucas et al. | |
| 10,170,935 B2 | 1/2019 | Baarman et al. | |
| 10,199,877 B2 | 2/2019 | Van Den Brink et al. | |
| 10,702,445 B2 | 7/2020 | Francois et al. | |

(Continued)

OTHER PUBLICATIONS

International Search Report, and Written Opinion for PCT Application No. PCT/US2020/056912 dated Apr. 1, 2021.

(Continued)

*Primary Examiner* — Rexford N Barnie
*Assistant Examiner* — Terrence R Willoughby
(74) *Attorney, Agent, or Firm* — Patterson Thuente IP

(57) ABSTRACT

Systems and methods for improved wireless recharging efficiency and decreased processing requirements are described. A plurality of duty cycle/input voltage pairs are stored in a recharger, corresponding to three subsets: a first subset corresponding to a constant minimum input voltage and an increasing duty cycle; a second subset corresponding to a constant duty cycle and an increasing input voltage; and a third subset corresponding to a maximum input voltage and an increasing duty cycle.

13 Claims, 8 Drawing Sheets

(56) References Cited

U.S. PATENT DOCUMENTS

| | | | |
|---|---|---|---|
| 10,702,699 B2 | 7/2020 | Weiss et al. | |
| 2002/0029036 A1 | 3/2002 | Goble et al. | |
| 2009/0174263 A1* | 7/2009 | Baarman | H02M 3/33523 |
| | | | 307/104 |
| 2012/0083718 A1 | 4/2012 | Alleman et al. | |
| 2012/0262108 A1 | 10/2012 | Delisi et al. | |
| 2014/0049177 A1* | 2/2014 | Kulczycki | H05B 47/105 |
| | | | 315/209 R |
| 2014/0366306 A1* | 12/2014 | Clothier | A47L 9/2831 |
| | | | 15/377 |
| 2015/0028794 A1 | 1/2015 | Flett | |
| 2015/0194814 A1 | 7/2015 | Taylor et al. | |
| 2016/0248280 A1 | 8/2016 | Ben-Shalom et al. | |
| 2017/0214433 A1 | 7/2017 | Redman-White | |
| 2017/0358954 A1 | 12/2017 | Ren | |
| 2017/0361117 A1 | 12/2017 | Aghassian et al. | |
| 2018/0043167 A1* | 2/2018 | Gaddam | H02J 7/007192 |
| 2018/0101861 A1 | 4/2018 | Angara et al. | |
| 2019/0321645 A1 | 10/2019 | Jiang et al. | |
| 2020/0001094 A1 | 1/2020 | Iyer et al. | |
| 2020/0001095 A1 | 1/2020 | Iyer et al. | |
| 2020/0206515 A1 | 7/2020 | Faltys et al. | |

OTHER PUBLICATIONS

Li et al., An Efficient Topology for Wireless Power Transfer over a Wide Range of Loading Conditions, Jan. 2018, 16 pages, MDPI, Energies (Basel, Switzerland) as available at https://www.mdpi.com/1996-1073/11/1/141.

* cited by examiner

SELF TUNING CLASS D DRIVER FOR MAXIMUM POWER FACTOR IN WIRELESS RECHARGER

CROSS-REFERENCE TO RELATED APPLICATIONS

This application claims the benefit of U.S. Provisional Application No. 62/925,487, filed on Oct. 24, 2019, the entirety of which is incorporated herein by reference.

FIELD

The present technology is generally related to an implantable medical device and more specifically a wirelessly rechargeable implantable device that delivers a medical therapy.

BACKGROUND

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices include neuro stimulators, drug delivery pumps, pacemakers, defibrillators, diagnostic recorders, and cochlear implants. Some implantable medical devices provide therapies with significant power demands. To reduce the size of the power source and to extend the life of the power source, some of these implantable devices can be recharged while implanted with a transcutaneous recharge signal produced by one or more field-producing coils external to the patient.

In order to recharge such devices efficiently, various characteristics of both the device itself and the recharger can be adjusted. Inductive recharge requires control of oscillating current in a coil. For a frequency range of 8-120 kHz, which is typical for implanted medical devices, coil size (and therefore impedance) is determined by maximizing patient ease of use. In general, it is preferable to put the recharger in proximity to the rechargeable device, to maximize power transfer rate, and to prevent overheating both of the device itself and of the recharger that can be uncomfortable or injurious to the patient. These goals can be accomplished by both mechanical solutions (such as devices that detect, position, and/or hold rechargers near to the implanted device, or use of larger recharging coils in the recharger, the implanted device, or both) and electronics (such as devices that modify the field strength, depth, direction, from the recharger, or that make efficient use of the field at the implanted device itself, or other mechanisms to promote more efficient charging).

In general it is preferable to most patients to minimize the obtrusiveness of the recharger by making recharging devices and implanted devices smaller. This objective, however, can be at odds with the goal of increasing recharging speed, which is typically improved by increasing coil size. While larger charging coils can help accomplish faster or more efficient recharge, they can result in larger devices. While additional power sources could be implemented, conventional devices typically use a single lithium ion battery, such that increasing the output voltage is accomplished by use of a variable boost mode converter that supplies a class D amplifier with power. Without adding additional power sources, the power output is therefore limited by the maximum power output of the battery, as delivered by the coil and the variable boost. To achieve commercially desirable coil currents using realizable boost voltages, gain can be added using a resonating LC tank circuit.

Small devices—even efficient ones—also present challenges for heat dissipation. Similarly, increasing the depth of implantation of a device is generally preferred by patients, but a deeper implant can require a recharger coil that generates a higher level of electromagnetic field, which typically requires higher operating voltage. As such, the recharger may need to be larger, which is generally not preferred by patients.

In response to these constraints, known systems and methods include setting duty cycle to scale the bridge voltage by a percentage, which controls voltage output while maintaining constant bridge voltage. This scaling can be accomplished by using a secondary circuit and adjusting duty cycle to maintain resonance frequency.

Creative solutions that balance or overcome the contradicting consumer preferences are needed, such as solutions that provide higher field strengths without requiring larger rechargers or larger implanted devices. Smaller size devices should be developed that do not overheat, while still providing high recharging efficiency at a variety of operating conditions.

SUMMARY

The techniques of this disclosure generally relate to wireless charging improvements by dynamic adjustment of a recharger characteristic that is a function of both duty cycle and operating voltage. According to a first embodiment, a system for wirelessly recharging a battery-powered device includes a recharger coil, a tank circuit electronically coupled to the recharger coil to selectively power the recharger coil, and a zero-voltage crossing circuit configured to detect a voltage at the recharger coil. A processor is coupled to the recharger coil, the tank circuit, and the zero-voltage crossing circuit. The processor is configured to power the tank circuit at an input power level and a duty cycle based upon the detected voltage at the recharger coil and a predetermined output level.

Optionally, the system can additionally include a memory coupled to the processor, the memory comprising a lookup table of a plurality of duty cycle/input voltage pairs, each of the duty cycle/input voltage pairs corresponding to one of a plurality of predetermined output levels. The plurality of duty cycle/input voltage pairs can be selected from any of three subsets: a first subset corresponding to a constant minimum input voltage and an increasing duty cycle; a second subset corresponding to a constant duty cycle and an increasing input voltage; and a third subset corresponding to a maximum input voltage and an increasing duty cycle. The duty cycle of the second subset can be 0.371. The system can include a frequency sense circuit.

According to another embodiment, a method for wirelessly recharging a battery-powered device is disclosed. The method includes selecting a desired power output level of a wireless recharger having a recharger coil, a tank circuit, a zero-voltage crossing circuit, a memory, and a processor; detecting a voltage of the recharger coil with the zero-voltage crossing circuit; selecting one of a plurality of duty cycle/input voltage pairs stored in the memory that correspond to the desired power output level; and driving the tank circuit at the one of the plurality of duty cycle/input voltage pairs selected by the processor, which causes the recharger coil to be powered.

The duty cycle/input voltage pairs can be arranged in three subsets: a first subset corresponding to a constant minimum input voltage and an increasing duty cycle; a second subset corresponding to a constant duty cycle and an increasing input voltage; and a third subset corresponding to a maximum input voltage and an increasing duty cycle. The duty cycle of the second subset can be 0.371.

According to another embodiment, a recharger includes a primary coil configured to emit a recharge signal. The recharger includes a frequency sense circuit configured to detect the frequency of a voltage in the primary coil, a zero-crossing circuit configured to detect whether the voltage in the primary coil is positive or negative, a processor configured to receive the frequency of the voltage from the frequency sense circuit and the detection of whether the voltage is positive or negative, and output a series of pulses at an input voltage. A width of each one of the series of pulses is based upon a duty cycle determination; and a frequency of the series of pulses is based upon the frequency of the voltage detected by the frequency sense circuit. A memory comprising a series of effective voltages, each of the effective voltages corresponding to a power factor of the recharger, and each of the effective voltages further corresponding to a duty cycle and an input voltage. The series of effective voltages include a first subset corresponding to a constant minimum input voltage and an increasing duty cycle; a second subset corresponding to a constant duty cycle and an increasing input voltage; and a third subset corresponding to a maximum input voltage and an increasing duty cycle.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
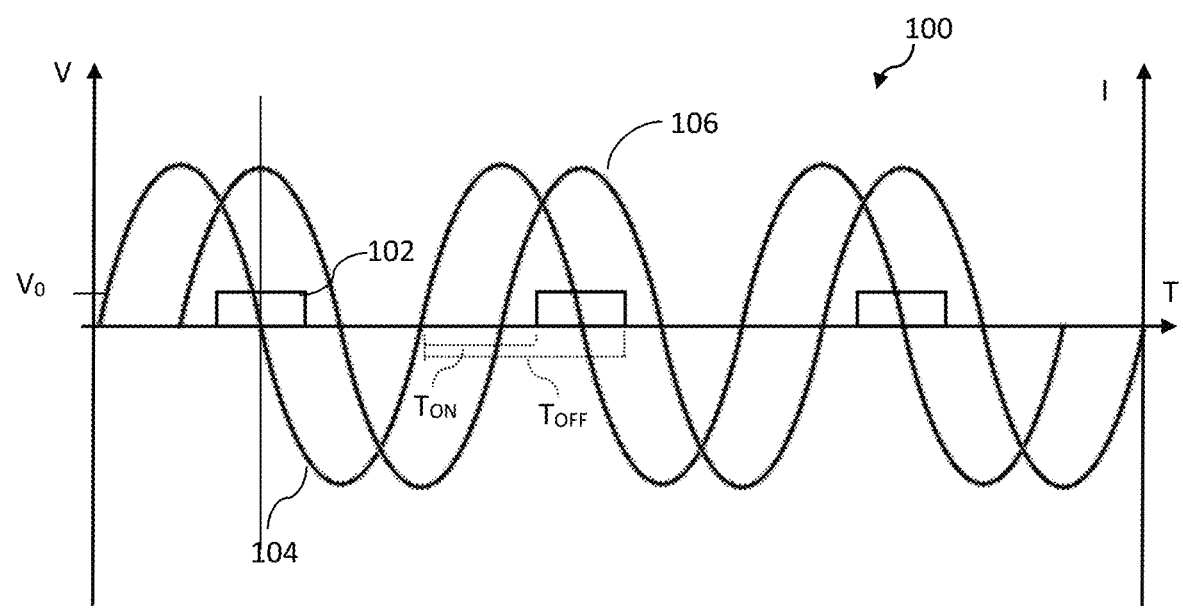
FIG. 1 is a graph of voltage and current in a recharger, according to an embodiment.

Embodiments disclosed herein provide input voltage/duty cycle combinations that improve operating efficiency while decreasing computational and processing requirements for a recharger system. More particularly, the embodiments disclosed herein provide pairs of input voltage and duty cycle that fall along three discrete ranges: a first range with voltage at an operational minimum and increasing duty cycle; a second range with a set duty cycle and increasing operating voltage; and a third range with a maximized input voltage and increasing duty cycle.

As described above, modifying the recharging field for an implanted device can present tradeoffs whereby improving one desired characteristic (such as size, efficiency, or charging speed) can adversely affect another. For example, increasing a recharge field strength or duty cycle can accomplish the goals of reaching a deeper-implanted device or faster recharge, respectively, but they can come with the tradeoff of requiring larger batteries to boost the emitter coil voltage to a sufficient level, or of decreased efficiency of the recharging system. Accordingly, devices and methods for operating them are disclosed herein that provide highly efficient recharge without requiring larger rechargers or implanted devices.

These goals are accomplished by modifying a parameter, referred to herein as effective voltage $V_{eff}$. A recharger according to embodiments described herein provides a square wave to the tank circuit that drives the recharger coil at a voltage between a minimum ($V_{MIN}$) and a maximum ($V_{MAX}$). The recharger's square wave is driven with a duty cycle D that ranges between 0 and 0.5, as described in more detail below with respect to FIG. 2.

Traditionally, input voltage V and duty cycle D have each been limited by one another, and there is a tradeoff between boost voltage and duty cycle (i.e., lower duty D cycle can result in higher boost voltage V for the smaller portion of the period that the voltage is "on"). As described in more detail below, we have recognized that a power factor $\lambda$ (see Eq. 1) can be maximized, and by continuously monitoring resonant frequency the two factors V and D can be controlled as a single variable $V_{eff}$ that enhances efficiency compared to conventional systems. Hardware in the coil driver circuit can be monitored by software arranged in a microcontroller to ensure that boost voltage V and/or duty cycle D are updated as needed to precisely control a desired level of recharge power.

As an initial matter, it has been recognized that the tank circuit for rechargers acts as a high-Q bandpass filter that accepts the first harmonic and attenuates all others to negligible levels. Thus to promote efficiency, it would be desirable to maximize the first harmonic of the signal in a tank circuit, $V_{eff}$. $V_{eff}$ is controlled to maintain maximum possible power factor $\lambda$, defined in Equation 1:

$$\lambda = \frac{V_{eff}}{V_{rms}} \qquad \text{Eq. 1}$$

Increasing or maximizing the power factor $\lambda$ provides several advantages, including insensitivity to slight variation in duty cycle and greater measurement accuracy.

FIG. 1 is a chart 100 that depicts voltage and current in a tank circuit related to resonant frequency detection. Pulse 102 is a voltage pulse applied to a tank that drives a recharger coil. Pulse 102 is a square wave that steps between a voltage of 0 and an operating voltage $V_O$. Recharger coil voltage 104 depicts the voltage in the primary coil that emits signal to a corresponding implanted device. Recharger current 106 is induced current, which lags recharger coil voltage 104 by 90°.

The operating voltage $V_O$ can be set up to a maximum operating voltage based on the battery (or other power supply) and a variable boost. The duty cycle D is based upon the difference between $T_{ON}$ and $T_{OFF}$. $T_{ON}$ is defined as the amount of time between the recharger coil voltage 104 becoming positive and the transition of pulse 102 from 0 to $V_0$. TOFF is defined as the amount of time between the recharger coil voltage 104 becoming positive and the transition of pulse 102 from $V_0$ to 0. Detection of these time periods can be accomplished in practice by, for example, implementing a zero detection circuit that outputs a signal that is 1 when recharge coil voltage 104 is greater than zero and 0 when recharge coil voltage 104 is less than zero.

Figure 2:
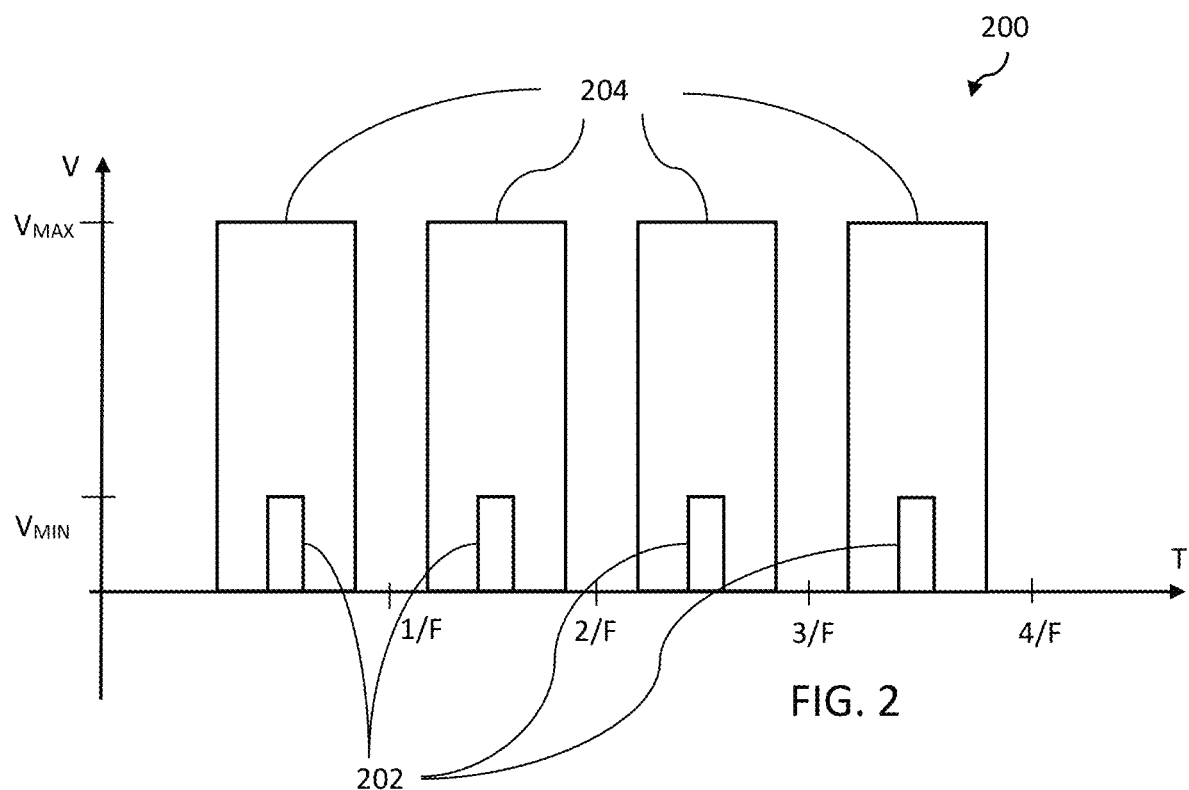
FIG. 2 depicts maximum and minimum voltage and duty cycle values, according to an embodiment.

FIG. 2 is a chart 200 depicting minimal drive voltage waveform 202 and maximal drive voltage waveform 204. As described above, in theory the duty cycle D can vary from 0.1 to 0.5, and the effective voltage can vary up to a maximum set by the power supply and also based upon the duty voltage D (i.e., a lower duty D requires higher $V_O$ for the same $V_{eff}$).

In practice, however, constraints are set upon the duty voltage and the operating voltage that ensure efficient charging. In chart 200, the constraints on maximum voltage are based upon the upper end of a boost regulator's range, and the constraints on minimum voltage can be based upon dropout voltage of components within the circuitry, for example. Although different circuitry will have different voltage ranges based on their inherent characteristics, an example voltage range could be from a minimum of about 1V to a maximum of about 20V, or more particularly from about 7.5V to about 17.5V. The minimum voltage is shown in chart 200 as the height of the minimal drive voltage waveform 202, and the maximum voltage is shown in chart 200 as the height of the maximal drive voltage waveform 204.

Duty cycle is also bounded, as shown in chart 200. The maximum duty cycle is chosen to prevent reduction in the effective voltage applied to the tank. The minimum duty cycle is set based on the particular characteristics of the recharger circuitry in order to provide sufficient current samples for the device to conduct current sampling accurately. More rapid sampling thus enables shorter duty cycles. In embodiments, duty cycle can range from about 0.05 to about 0.75, or more particularly from about 0.1 to about 0.5, or even more particularly from about 0.2 to about 0.5. The minimum duty cycle is shown in chart 200 as the percentage of the time T in which minimal drive voltage waveform 202 is nonzero, and the maximum duty cycle is shown in chart 200 as the percentage of the time T in which the maximal voltage 204 is nonzero.

In an embodiment, to start oscillation the resonant frequency of a tank circuit can be guessed. The tank is initially driven at that frequency in fixed frequency mode and then driven in an "autotune" mode. In an embodiment, the tank driver is a half-bridge circuit, and excitation is therefore applied for half the period at most. The tank then relaxes at its resonant frequency for the remainder of the period. Thus, even in fixed frequency mode, the tank will naturally adjust its frequency by a minimum of half the difference between drive frequency and resonant frequency every period.

Figure 3A:
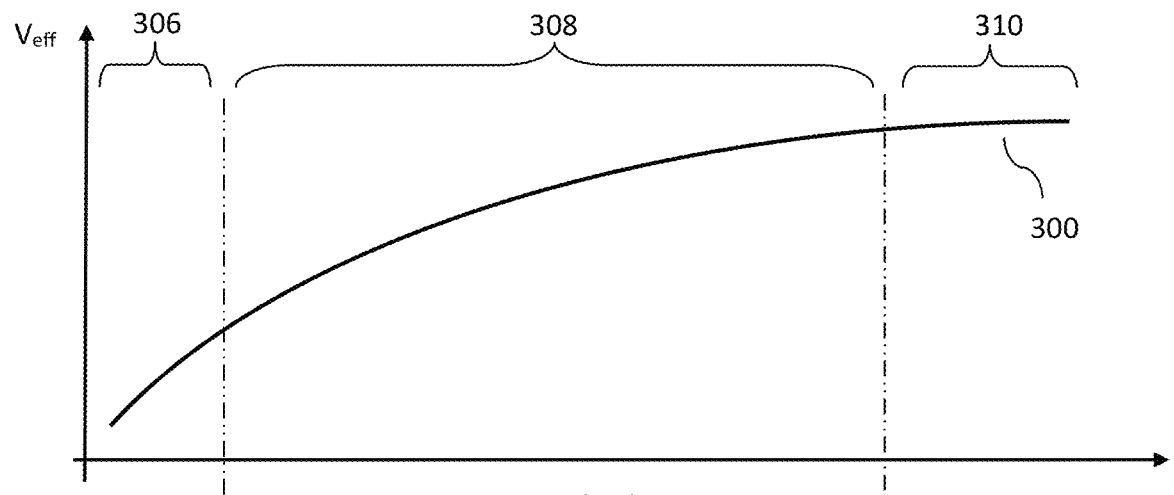
FIGS. 3A-3C show effective voltage as a function of duty cycle and input voltage, according to an embodiment.
Figure 3B:
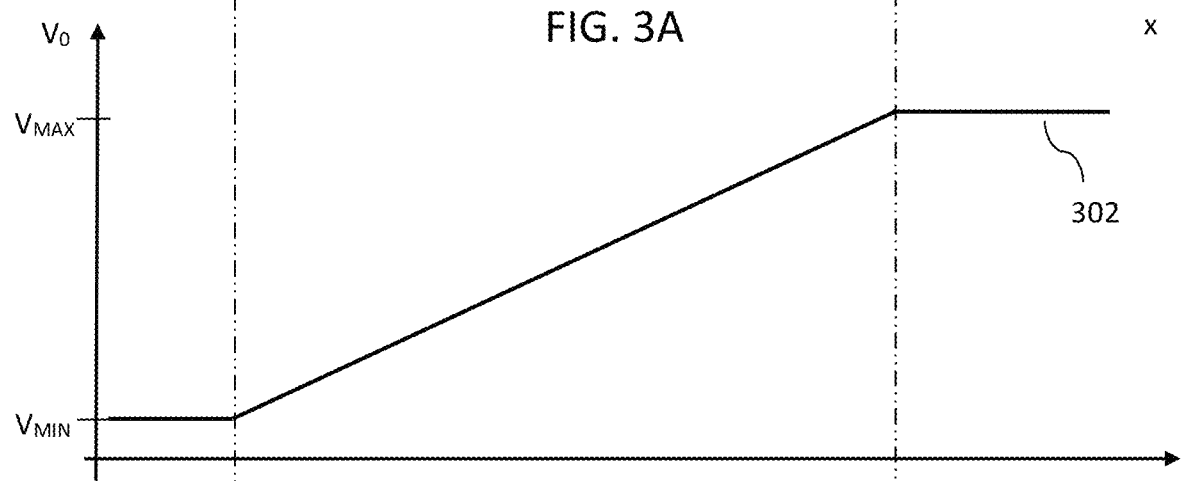
Figure 3C:
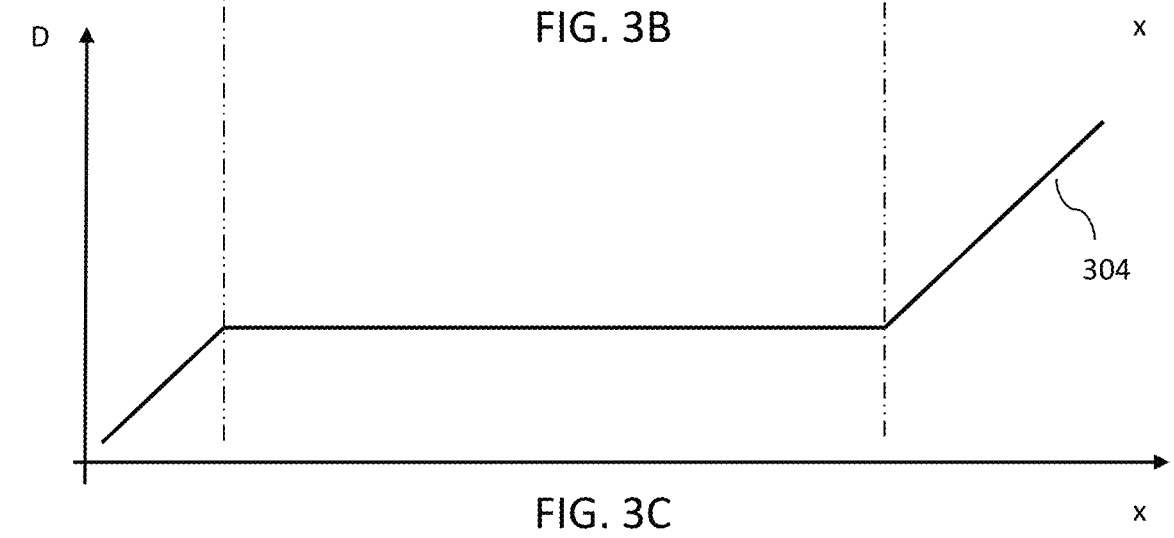

FIGS. 3A-3C depict effective voltage $V_{eff}$, operating voltage $V_0$, and duty cycle D, respectively, according to an embodiment.

As described above, square voltage waveforms (e.g., pulse 102 of FIG. 1, which can range in size from minimal drive voltage waveform 202 to maximal drive voltage waveform 204 of FIG. 2) are applied to a tank circuit, which acts as a high-Q bandpass filter. The bandpass accepts the first harmonic and attenuates all other harmonics to negligible levels. The voltage square wave (e.g., 102) can be decomposed into a Fourier series based on operating voltage $V_0$ and duty cycle D at frequency F:

$$V(t) = V_0 D + \sum_{k=1}^{\infty} \frac{2V_0 \sin(k\pi D)}{k\pi} \cos(2\pi k F t)$$

such that the first harmonic (i.e., the component not attenuated by the tank circuit) is $$\frac{2V_0 \sin(\pi D)}{\pi} \cos(2\pi F t)$$

the RMS magnitude of this term is therefore:

$$V_{eff} = \frac{\sqrt{2}}{\pi} V_0 \sin(2\pi F t) \qquad \text{Eq. 2}$$

As shown in Eq. 2, the effective voltage $V_{eff}$ that maximizes the first harmonic is based on both input voltage $V_0$ and duty cycle D. Veff is the direct connection between power and current of the tank ($P_{TANK}$ and $I_{TANK}$, respectively), such that:

$$P_{TANK} = I_{TANK} V_{eff} = \frac{V_0 I_0}{\pi} \sin(\pi D)$$

Returning to FIG. 3, $V_{eff}$ is shown in FIG. 3A. $V_{eff}$ curve 300 is a function of both operating voltage ($V_0$ curve 302, shown in FIG. 3B) and duty cycle (D curve 304, shown in FIG. 3C). The three charts in FIGS. 3A-3C share a common axis, indicated as x. FIG. 3 is separated into first region 306, second region 308, and third region 310, each corresponding to a different range of x.

In practice, depending upon a desired effective voltage $V_{eff}$, firmware in a recharger can select an appropriate x that will provide the desired output, while avoiding computations and improving system performance and efficiency relative to conventional devices. The path shape of $V_{eff}$ 300 is chosen to meet two main criteria. First, the number of points at which the system operates at low duty cycle are minimized. As such, increasing $V_{eff}$ from low values is accomplished in region 306 by first increasing D curve 304, while leaving $V_0$ curve at its minimum value. Second, as described above in Eq. 1, power factor λ should be maximized. Combining Eq. 1 and Eq. 2, it can be shown that:

$$\lambda = \frac{\sqrt{2} \sin(\pi D)}{\pi \sqrt{D}}$$

which is maximized at a value of D=0.371.

As such, second region 308 maintains constant duty cycle D at the maximum value of 0.371, while operating voltage is increased as shown by the linear ramp of $V_0$ curve 302. Once $V_0$ curve 302 has increased from its minimum operating voltage $V_{MIN}$ to its maximum operating voltage $V_{MAX}$, duty cycle remains the only available mechanism for further increasing $V_{eff}$. This is shown in third region 310, in which $V_0$ curve 302 is at its maximum $V_{MAX}$, while D curve 304 is increased to result in $V_{eff}$ curve 300 rising to its peak value.

Setting duty cycle and operating voltage to achieve a desired effective voltage as shown in FIGS. 3A-3C provides several advantages. As an initial matter, tank voltage is least sensitive to slight variations of duty cycle when power factor λ is maximized. Second, since λ is easily measurable by power analyzers, it is relatively quick and straightforward for an operator to perform a performance check for maximized λ. Third, measurement accuracy improves with increasing power factor.

Figure 4:
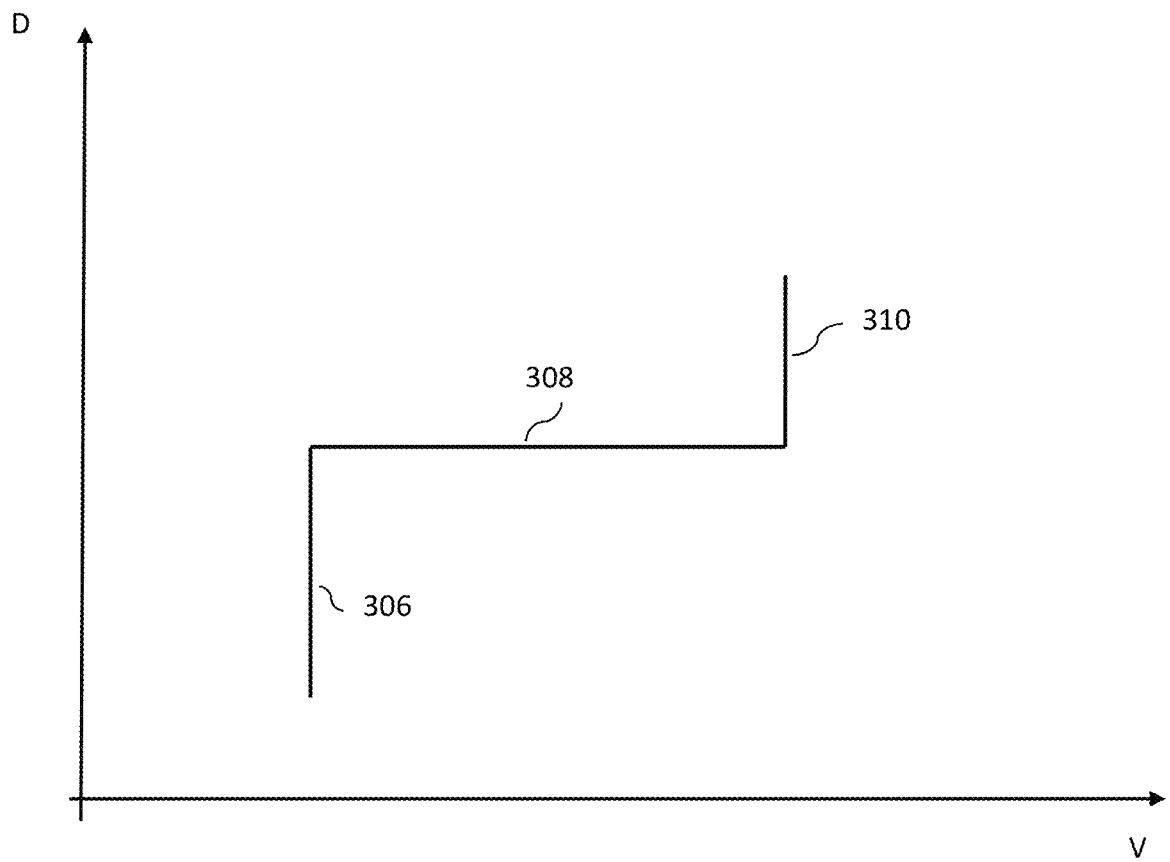
FIG. 4 shows the data of FIGS. 3A-3C on a chart of duty cycle vs. input voltage.

FIG. 4 shows the three regions 306, 308, 310 in another form, with voltage shown on the horizontal axis and duty cycle shown on the vertical axis. As shown in FIGS. 3A-3C and 4, for a desired effective voltage $V_{eff}$ a corresponding duty cycle D and operating voltage V0 can be selected by simply selecting the corresponding point "x." Returning to FIG. 1, the desired operating voltage $V_0$ and duty cycle D for a particular desired $V_{eff}$ can be set by tuning $T_{ON}$, $T_{OFF}$, and $V_0$. By measuring the period of the voltage output (104), the oscillation frequency F can be determined. $T_{ON}$ and $T_{OFF}$ are then set as follows:

$$T_{ON} = \frac{1-2D}{4F_{SENSE}}; T_{OFF} = \frac{1+2D}{4F_{SENSE}}$$

Frequency F varies over time based on environmental and operating conditions. The preceding equations are based on an assumption that the operating frequency F of the circuit remains constant, or alternatively that the actual operating frequency is detected with sufficiently high frequency to continuously adjust (or "autotune") $F_{SENSE}$. The frequency $F_{SENSE}$ can be sensed by a specialized circuit, according to an embodiment.

In one embodiment, the operating voltages and duty cycles that accomplish the objectives set forth in FIGS. 3A-3D and FIG. 4 are provided in a lookup table to a processor in the recharger. The processor can calculate $T_{ON}$ and $T_{OFF}$ based on the lookup table for $V_{eff}$. The table below is a simplified version of such a lookup table, having seven effective voltages $V_1$-$V_7$. A processor can select a desired effective voltage ($V_1$-$V_7$) and look up the corresponding duty cycle D and input voltage $V_0$. Each of the rows below corresponds to an "x" value in FIGS. 3A-3C:

| $V_{eff}$ | D | $V_0$ |
|---|---|---|
| $V_1$ | .15 | 7.5 |
| $V_2$ | .25 | 7.5 |
| $V_3$ | .371 | 7.5 |
| $V_4$ | .371 | 12.5 |
| $V_5$ | .371 | 17.5 |
| $V_6$ | .45 | 17.5 |
| $V_7$ | .45 | 17.5 |

In the table above, the first region (see FIGS. 3A-3C, 306) corresponds to effective voltages $V_1$-$V_3$, in which duty cycle D increases while input voltage $V_0$ remains constant at a minimum value (here, 7.5 volts). The second region (see FIGS. 3A-3C, 308) corresponds to effective voltages $V_3$-$V_5$, in which the duty cycle D remains at a constant value to maximize power factor λ and input voltage $V_0$ increases. The third region (see FIGS. 3A-3C, 310) corresponds to effective voltages $V_5$-$V_7$, in which the duty cycle D is increased above the point that maximizes power factor λ and the input voltage $V_0$ is at its maximum (here, 17.5 volts). It should be understood that while the example table above includes only seven effective voltages, in embodiments there could be hundreds or even thousands of $V_{eff}$ values, each paired with a corresponding duty cycle D and input voltage $V_0$.

As shown in FIG. 3A, the slope of $V_{eff}$ decreases with higher values of x. In other words, more $V_{eff}$ points are concentrated at the high end, providing higher resolution for $V_{eff}$ at higher power outputs. This is advantageous because, at higher power outputs, heat management becomes more important. It is desirable to be able to modify the power output more finely to provide as efficient and rapid recharging as possible, without exceeding a level that would cause discomfort or injury to the patient.

Embodiments of the present disclosure may be used with a variety of implantable medical devices, including but not limited to nerve stimulation devices (also known as neuro stimulators or neuromodulation devices), drug delivery pumps, cardiac pacemakers, defibrillators, or implantable cardioverter-defibrillators. In embodiments, neuromodulation devices may be used to stimulate a variety of nerves or associated tissues for treating a variety of conditions. Electrical stimulation may be delivered for spinal cord stimulation (SCS), peripheral nerve stimulation (PNS), peripheral nerve field stimulation (PNFS), deep brain stimulation (DBS), cortical stimulation (CS), pelvic floor stimulation, sacral nerve stimulation, tibial nerve stimulation, gastric stimulation, and the like.

Figure 5A:
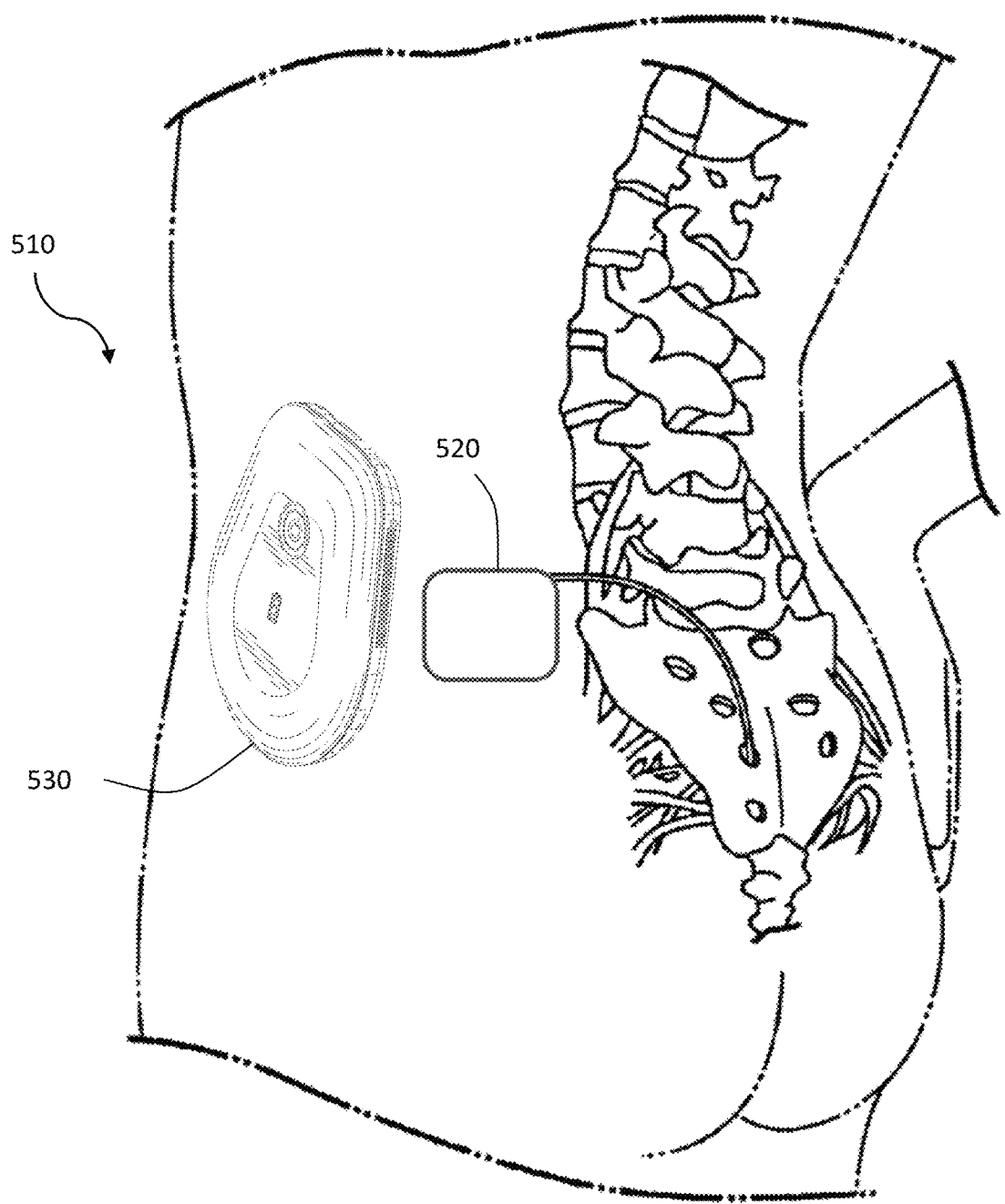
FIG. 5A is a schematic of a sacral nerve stimulation system according to an embodiment.
Figure 5B:
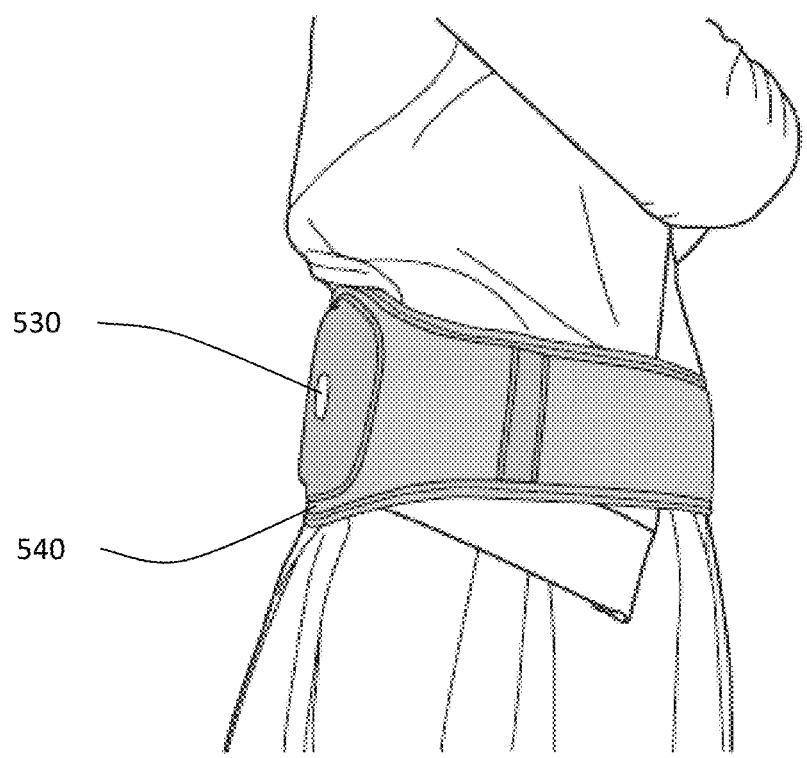
FIG. 5B is a schematic of a sacral nerve stimulation system with a wearable belt according to an embodiment.

In an example, embodiments of the present disclosure may be used as part of a system for treating pelvic health conditions including incontinence, overactive bladder, pelvic pain or other pelvic floor disorders. Referring to FIGS. 5A-B, embodiments of the present disclosure can be implemented as part of a sacral nerve stimulation system 510, including a rechargeable implantable nerve stimulation device 520 and an external recharger 530, wherein external recharger 530 can be positioned on or proximate to skin of the patient over the location of implantable nerve stimulation device 520 to facilitate recharging. Referring to FIG. 13B, external recharger 530 may also be wearable on the patient such as with a belt 540.

Figure 6:
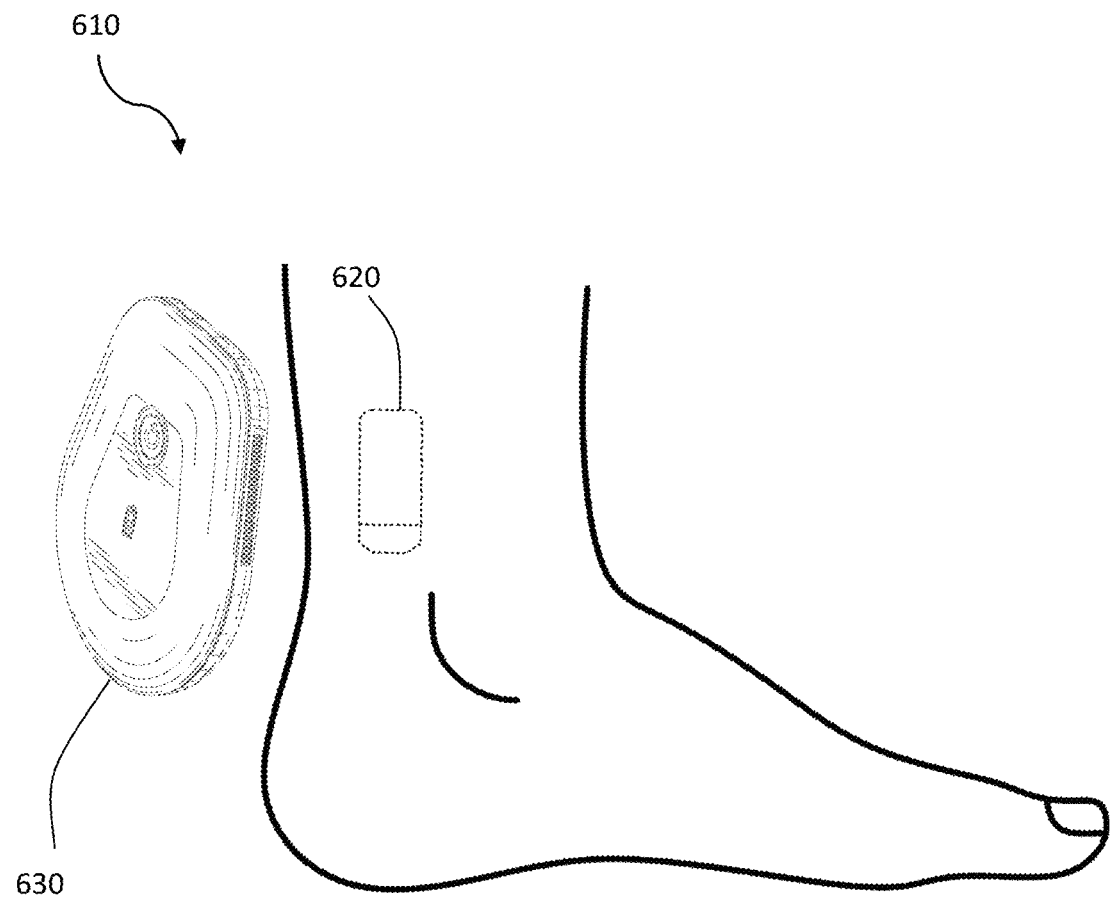
FIG. 6 is a schematic of a tibial nerve stimulation system according to an embodiment.
Figure 7:
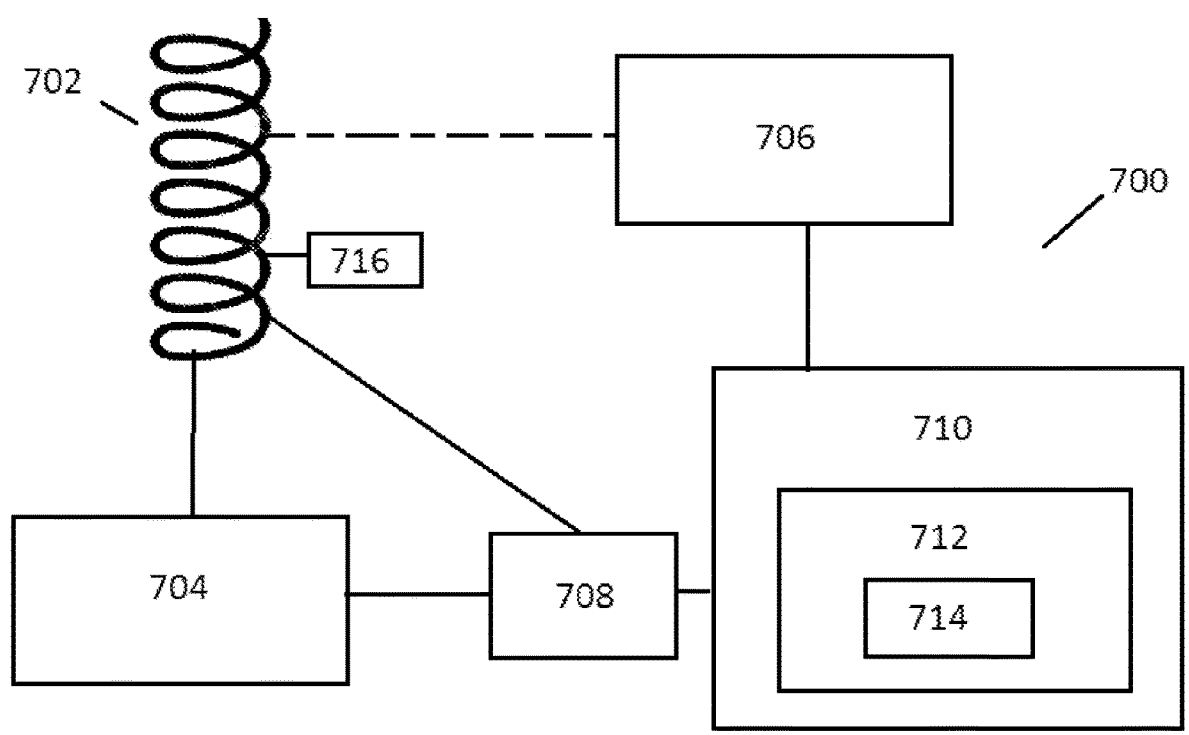
FIG. 7 is a simplified box diagram for wirelessly recharging a battery powered device according to an embodiment.

Referring to FIG. 6, in another example pertaining to treatment of pelvic health disorders, embodiments of the present disclosure may be implemented as part of a tibial nerve stimulation system 610, including an implantable tibial nerve stimulation device 620 and an external recharger 630, wherein external recharger 630 can be positioned on or proximate to skin of the patient over the location of implantable nerve stimulation device 620 to facilitate recharging. Tibial nerve stimulation system 610 may also include a wearable ankle cuff to hold external recharger 630 in position on an ankle of a patient.

In an example embodiment, a system 700 for wirelessly recharging a battery-powered device, the system comprising a recharger coil 702, a tank circuit 704 electronically coupled to the recharger coil 702 to selectively power the recharger coil 704, a zero-voltage crossing circuit 706 configured to detect a voltage at the recharger coil 702 and a processor 708 coupled to the recharger coil 702, the tank circuit 704, and the zero-voltage crossing circuit 706. In embodiments, the processor 708 is configured to power the tank circuit 704 at an input power level and a duty cycle based upon the detected voltage at the recharger coil 702 and a predetermined output level. A memory 710 coupled to the processor, the memory 710 comprising a lookup table 712 of a plurality of duty cycle/input voltage pairs 714, each duty cycle/input voltage pairs of the plurality of duty cycle/input voltage pairs 714 corresponding to one of a plurality of predetermined output levels.

In embodiments, the system can include a frequency sense circuit 716. In embodiments, the frequency sense circuit 716 is configured to detect a frequency of a voltage in the primary coil 702. The processor 708 configured to receive the frequency of the voltage from the frequency sense circuit 716 and the detection of whether the voltage is positive or negative, and output a series of pulses at an input voltage. A width of each one of the series of pulses is based upon a duty cycle determination. A frequency of the series of pulses is based upon the frequency of the voltage detected by the frequency sense circuit 716.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system for wirelessly recharging a battery-powered device, the system comprising:
    a recharger coil;
    a tank circuit electronically coupled to the recharger coil to selectively power the recharger coil;
    a zero-voltage crossing circuit configured to detect a voltage at the recharger coil;
    a processor coupled to the recharger coil, the tank circuit, and the zero-voltage crossing circuit, wherein the processor is configured to power the tank circuit at an input power level and a duty cycle based upon the detected voltage at the recharger coil and a predetermined output level; and
    a memory coupled to the processor, the memory comprising a lookup table of a plurality of duty cycle and input voltage pairs, each duty cycle and input voltage pair of the plurality of duty cycle and input voltage pairs corresponding to one of a plurality of predetermined output levels.

2. The system of claim 1, wherein the plurality of duty cycle and input voltage pairs comprise three subsets:
    a first subset corresponding to a constant minimum input voltage and an increasing duty cycle;
    a second subset corresponding to a constant duty cycle and an increasing input voltage; and
    a third subset corresponding to a maximum input voltage and an increasing duty cycle.

3. The system of claim 2, wherein the constant duty cycle of the second subset is between 0.1 and 0.5.

4. The system of claim 3, wherein the constant duty cycle of the second subset is 0.371.

5. The system of claim 1, further comprising a frequency sense circuit.

6. The system of claim 1, wherein the battery-powered device is an implantable medical device.

7. The system of claim 1, wherein the processor is configured to power the tank circuit by producing a period square wave.

8. A method for wirelessly recharging a battery-powered device, the method comprising:
    selecting a desired power output level of a wireless recharger having a recharger coil, a tank circuit, a zero-voltage crossing circuit, a memory, and a processor;
    detecting a voltage of the recharger coil with the zero-voltage crossing circuit;
    selecting, by the processor, one of a plurality of duty cycle and input voltage pairs stored in the memory that correspond to the desired power output level; and
    driving the tank circuit at the one of the plurality of duty cycle and input voltage pairs selected by the processor, which causes the recharger coil to be powered.

9. The method of claim 8, wherein the plurality of duty cycle and input voltage pairs comprise three subsets:
    a first subset corresponding to a constant minimum input voltage and an increasing duty cycle;
    a second subset corresponding to a constant duty cycle and an increasing input voltage; and
    a third subset corresponding to a maximum input voltage and an increasing duty cycle.

10. The method of claim 9, wherein the constant duty cycle of the second subset is between 0.1 and 0.5.

11. The method of claim 10, wherein the constant duty cycle of the second subset is 0.371.

12. The method of claim 8, wherein the battery-powered device is an implantable medical device.

13. The method of claim 8, wherein driving the tank circuit comprises producing a periodic square wave.

* * * * *